US 11,419,519 B2

(12) United States Patent
Kalantar-Zadeh et al.

(10) Patent No.: US 11,419,519 B2
(45) Date of Patent: Aug. 23, 2022

(54) GAS SENSOR CAPSULE

(71) Applicant: ROYAL MELBOURNE INSTITUTE OF TECHNOLOGY, Melbourne (AU)

(72) Inventors: Kourosh Kalantar-Zadeh, Albert Park (AU); Kyle Berean, Preston (AU); Nam Ha, Maidstone (AU); Jian Zhen Ou, Chadstone (AU)

(73) Assignee: ROYAL MELBOURNE INSTITUTE OF TECHNOLOGY, Melbourne (AU)

( * ) Notice: Subject to any disclaimer, the term of this patent is extended or adjusted under 35 U.S.C. 154(b) by 768 days.

(21) Appl. No.: 16/325,272

(22) PCT Filed: Aug. 14, 2017

(86) PCT No.: PCT/AU2017/000167
§ 371 (c)(1),
(2) Date: Feb. 13, 2019

(87) PCT Pub. No.: WO2018/032032
PCT Pub. Date: Feb. 22, 2018

(65) Prior Publication Data
US 2019/0183380 A1    Jun. 20, 2019

(30) Foreign Application Priority Data
Aug. 15, 2016   (AU) ................. 2016903219

(51) Int. Cl.
*A61B 5/07* (2006.01)
*A61B 5/00* (2006.01)
(Continued)

(52) U.S. Cl.
CPC ............. *A61B 5/073* (2013.01); *A61B 5/002* (2013.01); *A61B 5/1451* (2013.01);
(Continued)

(58) Field of Classification Search
CPC ....... A61B 5/073; A61B 5/002; A61B 5/1451; A61B 5/14539; A61B 5/14542;
(Continued)

(56) References Cited

U.S. PATENT DOCUMENTS 4,567,475 A * 1/1986 Bukowiecki ......... G08B 17/117
                                                340/634
5,019,885 A * 5/1991 Yagawara ............ G01N 27/123
                                                257/414
(Continued)

FOREIGN PATENT DOCUMENTS

CN      101460200 A    6/2009
CN      102517794 A    6/2012
(Continued)

OTHER PUBLICATIONS

Shin et al., Health care application of gas sensors—Medical devices of breath analysis—, Synthesiology English edition (Year: 2015).*
(Continued)

*Primary Examiner* — Jacqueline Cheng
*Assistant Examiner* — Tho Q Tran
(74) *Attorney, Agent, or Firm* — Nixon & Vanderhye

(57) ABSTRACT

A capsule adapted to be introduced into the digestive system and gastrointestinal (GI) tract of a mammal which consists of a capsule shaped container consisting of a wall material capable of being bio compatible with the digestive system and being adapted to protect the electronic and sensor devices contained in the capsule. The capsule contains gas composition sensors operable at several temperature points for a short duration, a temperature sensor, a micro controller, a power source and a wireless transmission device. The capsule wall incorporates gas permeable membranes adjacent said gas sensors. The microprocessor is programmed to receive data signals from the sensors and convert the signals
(Continued)

into gas composition and concentration data and temperature data suitable for transmission to an external computing device.

14 Claims, 6 Drawing Sheets

(51) Int. Cl.
*G01N 33/497* (2006.01)
*A61B 5/145* (2006.01)
*A61B 5/1491* (2006.01)

(52) U.S. Cl.
CPC ........ *A61B 5/1491* (2013.01); *A61B 5/14539* (2013.01); *A61B 5/14542* (2013.01); *A61B 5/4238* (2013.01); *A61B 5/4255* (2013.01); *A61B 5/6861* (2013.01); *G01N 33/497* (2013.01); *A61B 5/14507* (2013.01); *A61B 2562/0271* (2013.01); *A61B 2562/162* (2013.01)

(58) Field of Classification Search
CPC ... A61B 5/1491; A61B 5/4238; A61B 5/4255; A61B 5/6861; A61B 5/14507; A61B 2562/0271; A61B 2562/162; G01N 33/497
See application file for complete search history.

(56) References Cited

U.S. PATENT DOCUMENTS

| | | | | |
|---|---|---|---|---|
| 5,528,225 | A * | 6/1996 | Sakai | G01N 27/16 340/632 |
| 6,095,681 | A * | 8/2000 | Kunt | G01N 27/124 374/10 |
| 7,510,595 | B2 | 3/2009 | Freeman et al. | |
| 8,469,857 | B2 | 6/2013 | Harada | |
| 8,519,726 | B2 | 8/2013 | Sun | |
| 8,884,382 | B2 | 11/2014 | Stetter et al. | |
| 2004/0167257 | A1 | 8/2004 | Ryang | |
| 2009/0318783 | A1 | 12/2009 | Rohde et al. | |
| 2010/0294024 | A1 | 11/2010 | Kumar | |
| 2012/0136209 | A1* | 5/2012 | Kostenich | G01J 3/0272 600/109 |
| 2013/0289368 | A1 | 10/2013 | Covington et al. | |
| 2015/0011874 | A1* | 1/2015 | Amoako-Tuffour | A61B 5/065 600/424 |
| 2015/0031963 | A1 | 1/2015 | Wright et al. | |
| 2016/0349201 | A1 | 12/2016 | Graunke | |
| 2016/0367790 | A1* | 12/2016 | Belenky | A61B 5/073 |

FOREIGN PATENT DOCUMENTS

| | | |
|---|---|---|
| CN | 202654319 A | 1/2013 |
| CN | 103623410 A | 3/2014 |
| CN | 103930763 A | 7/2014 |
| EP | 1358926 A1 | 11/2003 |
| WO | 2011028342 A2 | 3/2011 |
| WO | WO-2013/003892 A1 | 1/2013 |
| WO | WO-2015/121312 A1 | 8/2015 |
| WO | WO-2016/033638 A1 | 3/2016 |

OTHER PUBLICATIONS

Ou, J. Z. et al., "Human intestinal gas measurement systems: in vitro fermentation and gas capsules." Trends in biotechnology 2015, vol. 33, pp. 208-213.
Mc Caffrey, C. et al., "Development of a wireless swallowable capsule with potentiostaticelectrochemical sensor for gastrointestinal track investigation", Sensors and Actuators B 2015, vol. 218, pp. 8-15.
Kalantar-Zadeh, K. et al., "Intestinal gas capsules: A proof-of-concept demonstration." Gastroenterology 2016, vol. 150, pp. 37-39.
Nakata, S. et al., "Evaluation of the responses of a semiconductor gas sensor to gaseous mixtures under the application of temperature modulation", Analyst. 2002, vol. 127, pp. 1642-1648.
Mikolajczyk, J. et al., "Detection of Gaseous Compounds with Different Techniques", Metrology and Measurement Systems. 2016, vol. 23(2), pp. 205-224.
Rai S.K. et al and Gow S.J. et al., "Ultrathin (~ 10nm) InN resistive gas sensor for selectivity of breath ammonia gas by using temperature modulation", Proceedings of the 11th IEEE Annual International Conference on Nano/Micro-Engineered and Molecular Systems (NEMS). 2016, April.
Ou, J. Z. et al., "Potential of in vivo real-time gastric gas profiling: a pilot evaluation of heat-stress and modulating dietary cinnamon effect in an animal model", Science Reports. 2016, vol. 6:33387, pp. 1-9.
Brauns, E. et al., "Temperature modulation of a catalytic gas sensor", 2014, Sensors, vol. 14, pp. 20372-20381.
International Search Report and Written Opinion issued in PCT/AU2017/000167, dated Oct. 27, 2017; ISA/AU.
Nour Majid et al, "Silver nanoparticle/PDMS nanocomposite catalytic membranes for H 2 S gas removal", Journal of Membrane Science, NL, vol. 470 pp. 346-355, XP055462306 [X] 1,2,8 * paragraph [0001] * [A] 3-7.
Nour Majid et al, "CNT/PDMS composite membranes for H2and CH4gas separation", International Journal of Hydrogen Energy, vol. 38, No. 25, pp. 10494-10501.
AI, Min et al., Carbon Nanomembrane s(CMNs) Supported by Polymer; Mechanics and Gas Permeation; Adv. Mater. 2014,26,3421-3426.

* cited by examiner

GAS SENSOR CAPSULE

CROSS REFERENCE TO RELATED APPLICATIONS

This application is a U.S. National Phase Application under 35 U.S.C. 371 of International Application No. PCT/AU2017/000167 filed on Aug. 14, 2017. This application is based on and claims the benefit of priority from Australian Patent Application No. 2016903219 filed Aug. 15, 2016. The entire disclosures of all of the above applications are incorporated herein by reference.

This invention relates to gas sensors useful in an ingestible sensor capsule for monitoring gases generated in the gastrointestinal (GI) tract of mammals including humans.

BACKGROUND TO THE INVENTION

While there are currently diagnostic tools available such as capsule endoscopy and breath analysers, there is no equipment for the analysis of the gas constituents in the gastrointestinal tract. There are many reports on the strong likelihood of the association of these gas constituents to different illnesses. However, due to lack of any suitable tool and the inconveniences that these measurements create for the patients, the potential of this area has yet to be fully realized.

A capsule camera (Pillcam™) is commercially available for visualizing the colon and evaluating polyps. There is also available SmartPill which is an ingestible capsule that measures pH, pressure and temperature during the passage through the gastrointestinal (GI) tract.

U.S. Pat. No. 8,469,857 discloses a method of diagnosing GI conditions by analysing gases in breath analysis.

Patent application WO2013/003892 discloses a capsule with gas sensors and a gas permeable membrane for use with ruminant animals.

Optical gas sensors (generally infrared—IR) are the most gas selective devices even developed and are also used in WO2013/003892 for ruminants. However, the size of such capsules is large and cannot be used for human. There is still no technology for fabricating a small IR based gas sensor that can be used for humans. The smallest pill dimension standard for human is OOO and none of the current optical technologies allow the development of such optical based gas capsules.

USA patent application 2009/0318783 discloses a computerised method analysing data from the GI tract using an ingestible capsule that contains a sensor and providing data on the measurement plotted against time.

USA patent application 2013/0289368 discloses an ingestible capsule with a gas detector to assist in diagnosing diseases of the GI tract.

A difficulty with prior art devices is the lack selectivity of the gas sensors. For instance, a pure PDMS membrane allows all gas species to permeate through. This may be acceptable when highly selective gas sensors are used. However, most available gas sensors are non-selective. For instance the current hydrogen ($H_2$) gas sensors are also sensitive to other gas species such as methane ($CH_4$). Such lack of specificity seriously compromises the accuracy of the measurements.

It is an object of this invention to provide gas sensors for a GI tract capsule that can detect multiple gases.

BRIEF DESCRIPTION OF THE INVENTION

To this end the present invention provides a gas spectrometer for detecting GI tract gases which includes a semiconductor gas sensor and a thermal conductive gas sensor each operated at different temperatures for a predetermined duration so that they are able to selectively detect oxygen, hydrogen, carbon dioxide and methane; both gas sensors operating under the control of a microprocessor programmed with software to differentiate between the gases.

By changing the operating temperature of the gas sensors become more or less sensitive to specific gases of the gut. By changing the heater temperature (changing the duration of heating), the gas sensor can act as a single element that produces different values to various gases depending on the duration of the heating. Each sampled value, at a time, can be considered a pixel for a pseudo spectrometer. This means, if the sensor is sampled twice a spectrum of two pixels is produced. If the sensor element is sampled 100 times, a spectrum of 100 pixels is generated. Each spectrum is more specific for the sensor element. In this invention, the simplest pseudo element, consisting of two pixels per sensor is presented. Semi conducting and thermal conductivity sensors are the base of the invention as they both show gas responses that are a strong and repeatable function of their operating temperatures.

Another advantage of the semi conductor and thermal conductive based sensors is their very small sizes (in the mm order range). As such, they are the best candidates as gas sensor elements in human gas sensor capsules of less than OOO capsule dimensions.

Both semiconductor and thermal conductive gas sensors operate under the control of a microprocessor preferably programmed with a pattern recognition software such as neural network software to differentiate between the gases.

The two gas sensors are preferably contained in one portion of an ingestible capsule sealed from the battery and electronic components. The outer surface of this portion of the capsule is composed of a selectively permeable membrane. The sensor surfaces are located above a micro heater so that the sensors are heated in a short duration of less than a second to two or more different temperatures, depending on the number of pixels to be acquired for each spectrum. The sensitivity to different gases varies according to the temperature and this in association with the neural network software enables the readings from the different data points to be clustered for identification of the gases.

The capsules include gas permeable membranes to assist in the selectivity of the sensors. These are preferably the membranes disclosed in WO2016033638.

In another aspect this invention provides a capsule adapted to be introduced into the digestive system and GI tract of a mammal which consists of a capsule shaped container consisting of a wall material capable of being bio compatible with the digestive system and being adapted to protect the electronic and sensor devices contained in the capsule;

said capsule containing the gas spectrometer described above, optionally a temperature sensor, a micro controller, a power source and a wireless transmitter;

the microprocessor being programmed to receive data signals from the sensors and convert the signals into gas composition and concentration data and temperature data suitable for transmission to an external computing device. Between the data acquisition times, the microcontroller switches of the heater to sensors and goes into sleep mode to save power.

When the capsule is in the body, a data receiver is kept in close proximity, usually less than 5 metres away, to continuously collect the data signals from the capsule during the hours in which the capsule passes through the stomach, small intestine and colon.

The gas sensor capsule allows an accurate identification of the target gases in situ, where they are produced, and assists in linking them with more certainty to the state of health, effect of diet, environmental influences and the presence of illnesses.

These capsules permit the whole gastrointestinal tract to be surveyed, not just the accessible parts. In addition, the procedure is non-invasive and capsules pass out of the body of the subjects at the end of the process.

Especially for human applications, after being swallowed, the "gas sensor capsule" will help gastroenterologists to survey human subjects' gas species and their concentrations in oesophagus, stomach, duodenum, jejunum, and ileum (small intestine), as well as the cecum, colon and rectum (large intestine). The capsule may also help in understanding the gas species produced in other mammalians and associate them with their diets, state of health and the volume of gas production (for gas mitigation or production efficiency increase). The device allows the possibility of accurately investigating and fully obtaining the correlations between the existing gas species and gastrointestinal medical illnesses. Establishing such correlations and accurately assessing the gas content of the digestive tract of individual subjects will help to reveal the effects of the existing microorganisms in the digestive tract and help prescribing correct medications, resulting in more accurate targeting of gastrointestinal illnesses. As such, the gas sensor capsule will be an invaluable tool for assessing health status, using non-invasive diagnostics.

The gas sensor capsule of this invention is a diagnostic and monitoring tool, which may be swallowed and has the capability of accurately sampling gas constituents throughout the entire gastrointestinal tract. Its advantages are high selectivity and sensitivity measurements of gas constituents along the tract.

DETAILED DESCRIPTION OF THE INVENTION

Preferred embodiments of the invention will be described with reference to the drawings in which.

Figure 2A:
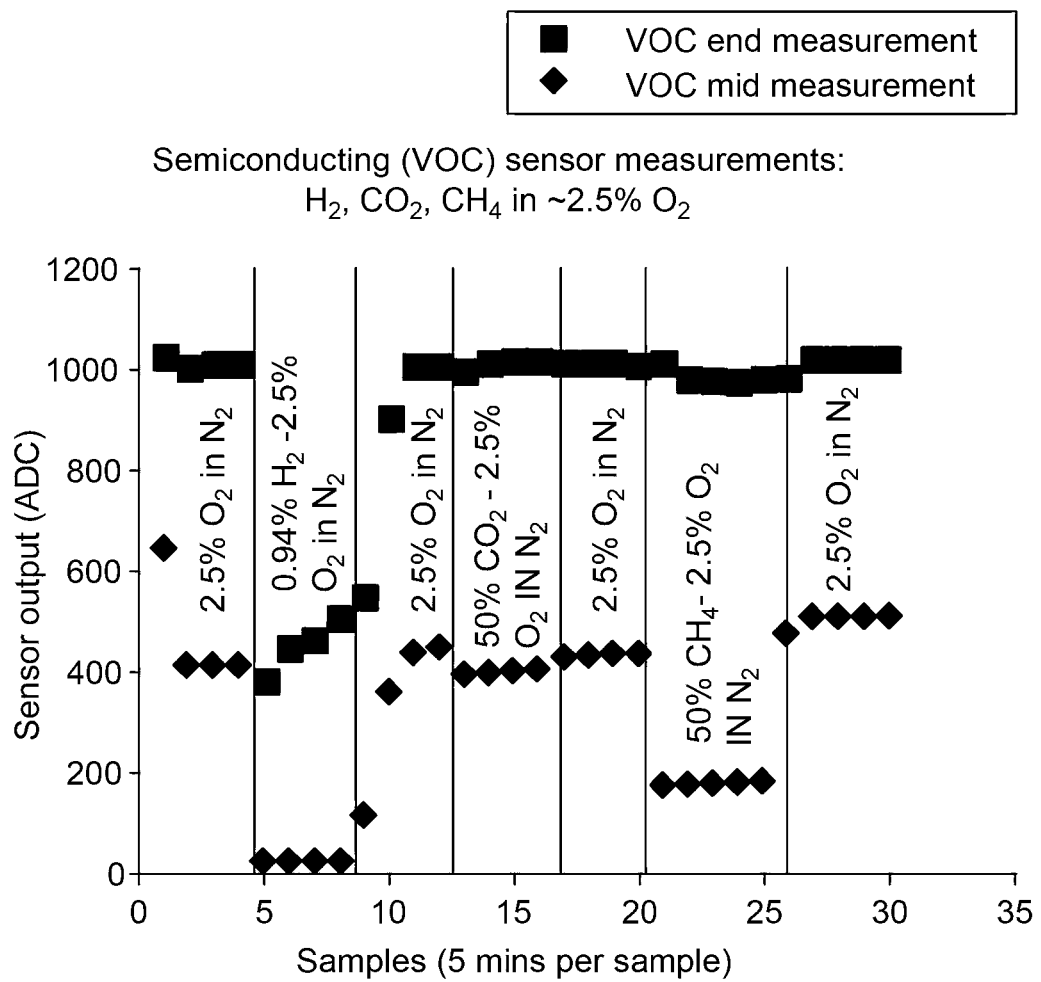
Figure 3:
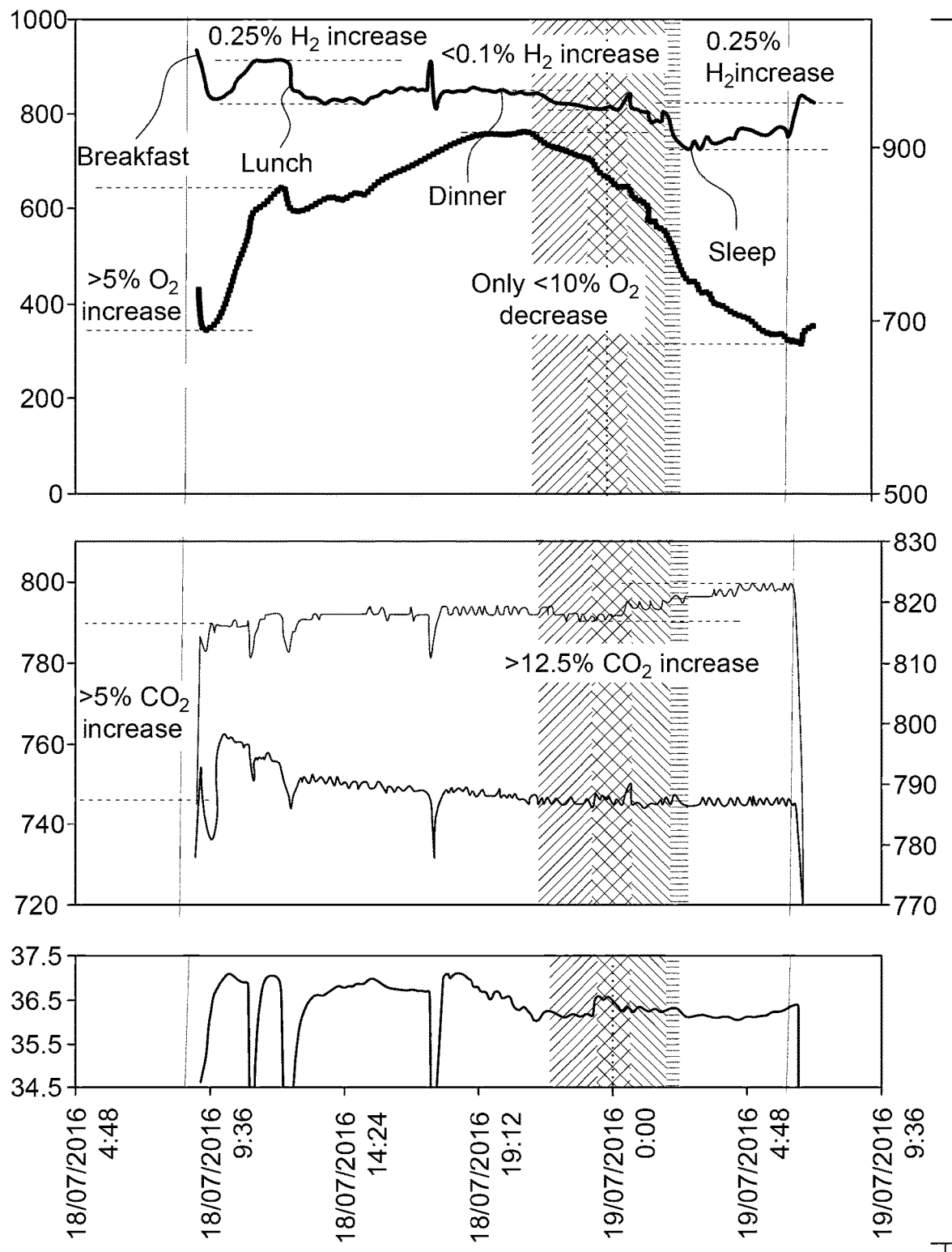
Figure 4:
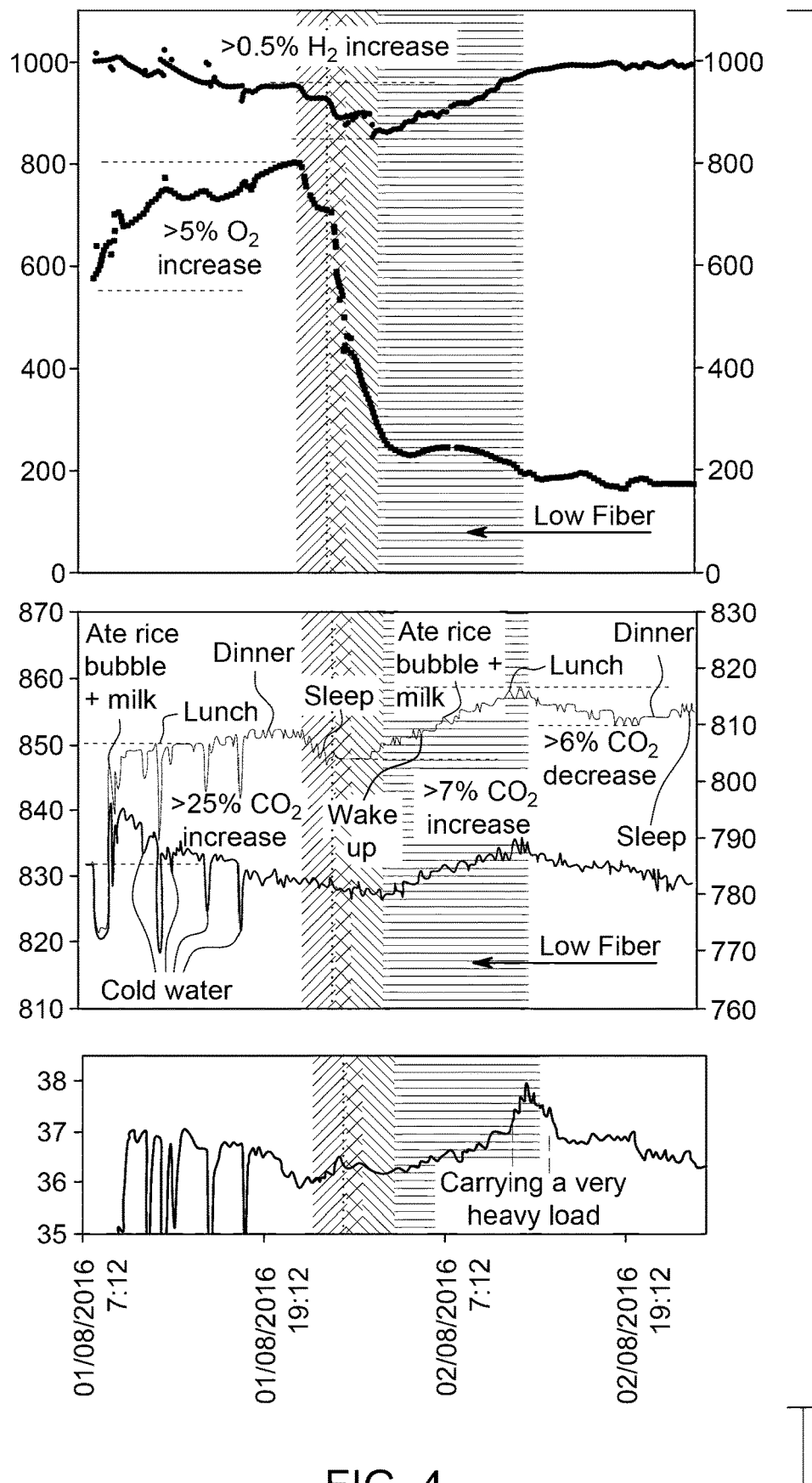

FIGS. 2A and B show response of two sensors to some typical gases of the gut for calibration;

FIG. 3 is the graphical output of data points from the two gas sensors over time, of a body response to a high fibre diet;

FIG. 4 is a graphical output from the two sensors of a body response to a low fibre diet.

Figure 1A:
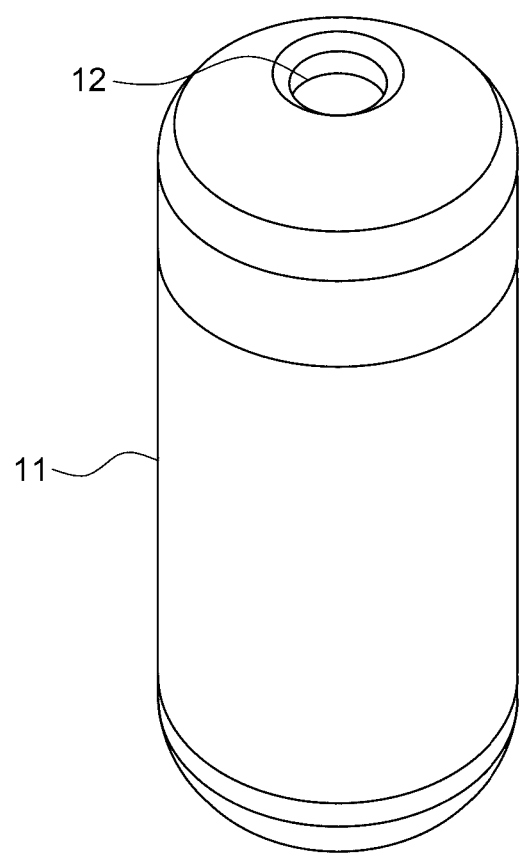
FIG. 1A is a schematic of a preferred capsule of this invention.
Figure 1B:
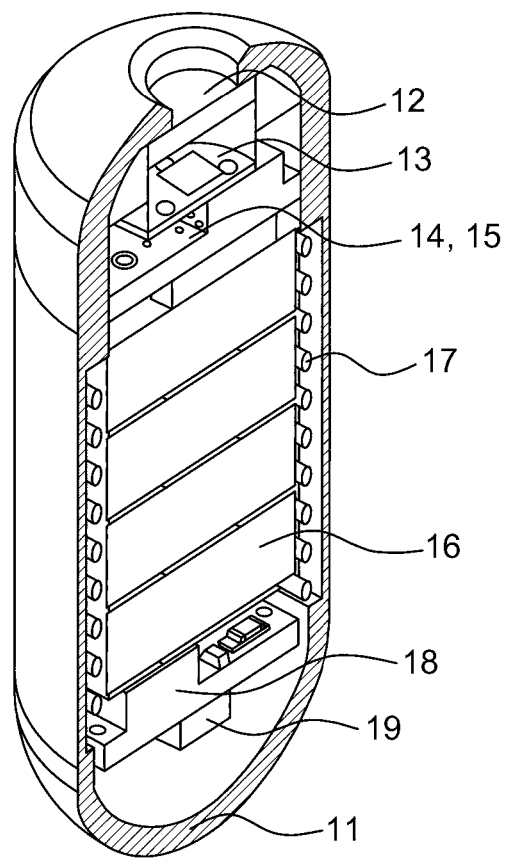
FIG. 1B is a cross sectional view of the preferred capsule.

The main components of a preferred capsule are illustrated in FIG. 1.

As shown in FIGS. 1A and B the typical capsule consists of a gas impermeable shell 11 which has an opening covered by a gas permeable membrane 12.

Internally the capsule includes a gas sensor 13, a temperature sensor 14, micro controller 15. The electronics also includes silver oxide batteries 16, an antenna 17, a wireless transmitter 18 and a reed switch 19.

Figure 2B:
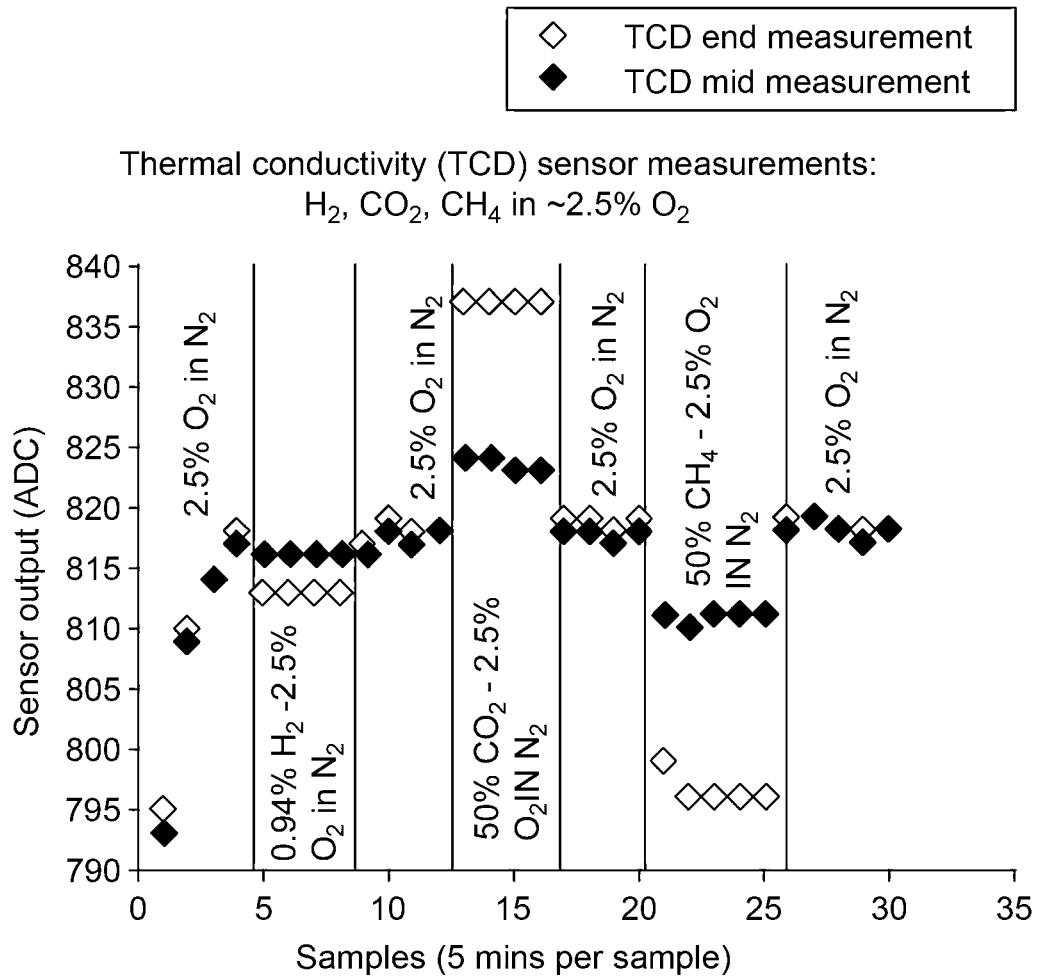

The main components of the capsule are:

Sensors 13: The two gas sensors are less than several mm in dimension each and are used to detect oxygen, hydrogen, carbon dioxide and methane. The anaerobic sensor is thermal conductor sensor and the aerobic sensor is a semiconductor sensor. The two gas sensors are contained in one portion of the capsule sealed from the battery and electronic components. The outer surface of this portion of the capsule is composed of a selectively permeable membrane. The sensor surfaces are located above a micro heater so that the sensors are heated in a short duration of less than a second to two or three different temperatures (the heating duration for the graph examples are shown in FIGS. 2A and 2B). The sensors are pre-calibrated, so that a sensor reading can be used to identify the composition and concentration of a particular gas. The sensitivity to different gases vary according to the operational temperature and this in association with the neural network or another pattern recognition software enables the readings from the different data points to be clustered for identification of the gases. As can be seen in FIG. 2 the sensors can show small cross-talks in sensing the gases. The increase in the number of sensors will help in extracting the exact response to each target gas using mathematical algorithms. For example, the semiconductor sensor may be heated to 150° C., 200° C. or 300° C. and is more sensitive to hydrogen at the lower temperatures and more sensitive to methane at the higher temperature (FIG. 2A). The semiconductor sensor is not sensitive to carbon dioxide. The thermal sensor is used to sense carbon dioxide as well as hydrogen and methane at two temperatures of 100° C. and 250° C. In mili second (ms) durations, 4 data points from the two sensors can be read and thus a continuous line graph of the concentrations may be produced.

Other gas sensors such as $NO_x$ and $H_2S$ as well as volatile organic compound sensors may be used.

In addition, a temperature sensor 14 is included. Other sensors such as pH sensors may be included to provide environmental information for the gas analysis.

The gas sensors are enclosed in a compartment of the capsule sealed from the electronic components. This compartment is enclosed by a gas permeable membrane 12 preferably a graphene polymer containing nanoparticles of silver to protect the surface from bacterial growth.

Electronic circuits 15, 18 (already available technology may be adapted): consists of a data acquisition system which switches between the sensors, and a coder and modulator that produce the digital data and sends it to the antenna 17 for transmission to the associated data receiver. Commercial bands (such as 433 MHz) are used for this application as electromagnetic waves in this frequency range can safely penetrate the human tissues. Other commercial bands may be used in various applications. Coding is required to assure that the unique data is sent from each individual capsule. The transmission antenna 17 is a pseudo patch type for transmitting data to the outside of the body data acquisition system. Power source 16 is a battery or super capacitor that can supply the power for the sensors and electronic circuits. A life time of at least 48 hours is required for digestive tract capsules. There may be less silver oxide batteries, depending on the needed life time and other specifications for the capsule.

The dimension of the capsule is preferably less than 1.1 mm in diameter and 2.6 mm in length to meet the OOO standard dimensions for human capsules. The body of the capsule is preferably made of indigestible polymer, which is biocompatible. The body is preferably smooth and non-sticky to allow its passage in the shortest possible time and reduces the chances of any capsule retention. An example of measurements that are conducted for calibrating the gas sensors is shown in FIGS. 2A and B. Semiconducting and thermal conductivity sensor measurements at different concentration of gases: (A) semiconducting (mid measurement is after 1 ms and end measurement after 7 ms) and (B) thermal conductivity (mid measurement is after 400 ms and end measurement after 1000 ms).

EXAMPLES

The signals from the capsule are shown in FIGS. 3 and 4.

High Fibre

The gas profiles of a human volunteer under high fibre diet is shown in FIG. 3. The dietary fibre intake was over 55 g per day. Capsule was taken at 9 am and left the body at 6 am the day after. The hatched areas are representative of the passage through different sections of the small intestine (duodenum, jejunum and ileum)

Low Fibre

The gas profiles of a human volunteer under low fibre diet are shown in FIG. 4. The dietary fibre intake was under 15 g per day. Capsule was taken at 9 am and left the body three days after that. Only the first two days are demonstrated. The hatched areas are representative of the passage through different sections of the small intestine (duodenum, jejunum and ileum)

The protein intake was kept under 2,200 cal for the volunteer of 82 kg weight. The volunteer was given three meals a day with snacks in between. The volunteer was allowed to continue the normal day to day routine.

Low and High Fibre

A volunteer was kept under a low and high fibre diet and the gas profiles were measured using the human gas capsules.

The volunteer was kept under the strict high or low fibre diet for two days prior to taking the capsule. The capsule was taken at 9 am of the third day and the diet was continued till the capsule left body.

High fibre diet: the volunteer was given high fibre food such as oat, nuts, lentil, bean and pear. The total fibre intake was over 55 g per day.

Low fibre diet: volunteer was given low fibre food such as white bread, white rice, cucumber, tomato, fish and chicken. The total fibre intake was kept under 15 g per day.

The output readings from each sensor are shown in FIGS. 3 and 4 and this demonstrates the variations in gas concentrations and body temperature in relation to the events noted on the figure.

The changes of the gas concentrations of the graphs were investigated using the neural network software and the sensor calibration data, to show the concentration of the gases oxygen, hydrogen, carbon dioxide and methane over the same time period as below.

Low Fibre Example: FIG. 4

$CO_2$ in the stomach was approximately 35%

Oxygen content in the stomach increased by 5% in the 17 hours that capsule was in the stomach $H_2$ is produced up to 0.5% in passage through the small intestine After passage through the small intestine $CO_2$ increased by 7% and then decreased by 6% during the day time After taking the high fibre food the $H_2$ concentration in the colon increased by more than 1.5%

A cycle is seen (bottom low fibre line 780 RHS axis) which is only sensitive to $CO_2$ and $CH_4$ (max at 12 pm and min at 10 pm)

High Fibre Example:

$CO_2$ in the stomach is approximately 50%

$O_2$ in the stomach increased by more than 5% with reference to the atmospheric concentration (21%) after the capsule was ingested 0.25% increase in the $H_2$ in stomach after taking a lentil salad for lunch $H_2$ is <0.1% in passage through the small intestine About 0.25% $H_2$ is in the colon $CO_2$ in the passage to the volunteers colon increased by 12.5%

The colon environment remains highly aerobic. The oxygen content seems to be over 10% in the colon region.

Benchmarking studies have been performed which compare the results of gas concentrations obtained through using: (i) the capsule and (ii) breath tests. Breath tests are the only other tool available using gas phase biomarkers as indicators of health. These studies showed that the capsule of the present invention significantly outperformed and more accurately identified the gas concentrations, for some gases by between 5,000 to 10,000 times when compared to the alternative breath tests.

Those skilled in the art will realise that this invention provides a valuable contribution to diagnosis of disorders in the human digestive system. It also generates information about the health status of humans and gas production in their digestive system. Those skilled in the art will also realise that this invention may be implemented in embodiments other than those described without departing from the core teachings of this invention.

The invention claimed is:

1. A capsule adapted to be introduced into and to pass through a digestive system and gastrointestinal tract of a mammal, the capsule comprising:
   a capsule shaped container including a capsule wall formed of wall material capable of being bio compatible with the digestive system and being adapted to protect electronic devices and gas sensors contained in the capsule;
   a microprocessor;
   a heater;
   a transmission antenna;
   the gas sensors comprising a semi-conductor gas sensor and a thermal conductive gas sensor each configured, under the control of the microprocessor and by changing a temperature setpoint of the heater, to take readings at two different operating temperature points for a predetermined duration to selectively detect one or more of hydrogen and methane in the readings of the semi-conductor gas sensor, and to selectively detect one or more of hydrogen, carbon dioxide and methane in the readings of the thermal conductive gas sensor; and
   the microprocessor programmed to control the operation of both of the gas sensors;
   the transmission antenna being configured, during passage of the capsule through the digestive system and gastrointestinal tract of the mammal, to continuously transmit data including the readings taken by both of the gas sensors to a data receiver external to the mammal.

2. The capsule as claimed in claim 1 in which the change of operational temperature alters the selectivity to said gases in the GI tract and the microprocessor is programmed with a pattern recognition software to differentiate between the gases.

3. The capsule as claimed in claim 1, wherein the gas sensors each include a sensor surface located above the heater to heat the sensors.

4. The capsule as claimed in claim 3, wherein the semi-conductor is heated to a temperature of 150° C., 200° C. or 300° C.

5. The capsule as claimed in claim 3, wherein the thermal sensor is heated to a temperature of 100° C. or 250° C.

6. The capsule as claimed in claim 1, wherein the semiconductor gas sensor and the thermal conductive gas sensor are pre-calibrated.

7. The capsule as claimed in claim 1, wherein the semiconductor gas sensor and the thermal conductive gas sensor are contained in a compartment of the capsule sealed from electronic components.

8. The capsule as claimed in claim 7, wherein the electronic components comprise:
   a data acquisition system for switching between the sensors;
   a coder and a modulator for producing a digital data signal; and
   an antenna for transmission to the associated data receiver.

9. The capsule as claimed in claim 7, wherein the outer surface of the sensor compartment is composed of a selectively permeable membrane.

10. The capsule as claimed in claim 1, wherein the capsule comprises a container including a wall comprising an indigestible biocompatible polymer.

11. The capsule as claimed in claim 1, further comprising a temperature sensor.

12. The capsule as claimed in claim 1 further comprising a pH sensor.

13. The capsule as claimed in claim 1, further comprising one or more sensors to selectively detect one or more of $NO_x$, $H_2S$, and volatile organic compounds.

14. The capsule as claimed in claim 1 adapted to continuously collect and send data signals to a data receiver.

* * * * *